United States Patent [19]

Cottrell et al.

[11] Patent Number: 5,087,792
[45] Date of Patent: Feb. 11, 1992

[54] PROCESS FOR THE DEHYDROGENATION OF HYDROCARBONS

[75] Inventors: Paul R. Cottrell, Arlington Heights; Michael E. Fettis, Prospect Heights, both of Ill.

[73] Assignee: UOP, Des Plaines, Ill.

[21] Appl. No.: 638,952

[22] Filed: Jan. 9, 1991

[51] Int. Cl.$^5$ .................................. C07C 5/32
[52] U.S. Cl. ........................... 585/661; 585/660; 502/34; 502/35; 502/38; 502/52; 502/53
[58] Field of Search .............. 585/654, 660, 661; 502/34, 35, 38, 50, 52, 53

[56] References Cited

U.S. PATENT DOCUMENTS

| | | | |
|---|---|---|---|
| 2,965,563 | 12/1960 | Steffgen et al. | 208/140 |
| 3,278,419 | 10/1966 | Coe et al. | 208/140 |
| 3,647,680 | 3/1972 | Greenwood et al. | 208/65 |
| 3,652,231 | 3/1972 | Greenwood et al. | 23/288 |
| 3,692,496 | 9/1972 | Greenwood et al. | 23/288 G |
| 4,148,749 | 4/1979 | Walden et al. | 585/418 |
| 4,159,938 | 7/1979 | Lewis | 208/140 |
| 4,507,397 | 3/1985 | Buss | 502/52 |
| 4,647,549 | 3/1987 | Greenwood | 502/37 |
| 4,980,325 | 12/1990 | Sechrist | 502/48 |
| 5,001,095 | 3/1991 | Sechrist | 208/140 |

Primary Examiner—Anthony McFarlane
Attorney, Agent, or Firm—Thomas K. McBride; John G. Tolomei; John G. Cutts, Jr.

[57] ABSTRACT

A process for the dehydrogenation of a hydrocarbon selected from the group consisting of propane and butane in the presence of a catalyst comprising platinum and a carrier material. Reconditioning of catalyst particles containing platinum by transferring the catalyst particles through a combustion zone, a drying zone and a re-dispersion zone improves the process. Drying of the catalyst particles immediately after the combustion of coke improves the operation of a platinum re-dispersion zone. The lower moisture content in the re-dispersion zone allows the equilibrium reaction between hydrogen chloride and oxygen on the one hand, and water and chlorine on the other hand to be shifted to the production of chlorine. This shift of the equilibrium reaction can be further improved by maintaining an oxygen-enriched environment within the platinum re-dispersion zone. The use of a much lower chloride concentration in the re-dispersion zone reduces the emissions of hydrogen chloride from the regeneration zone.

2 Claims, 2 Drawing Sheets

PROCESS FOR THE DEHYDROGENATION OF HYDROCARBONS

FIELD OF THE INVENTION

This invention relates to the art of catalytic conversion of hydrocarbons to useful hydrocarbon products. More specifically, it relates to a process for the dehydrogenation of hydrocarbons.

BACKGROUND OF THE INVENTION

Catalytic processes for the conversion of hydrocarbons are well known and extensively used. Invariably the catalysts used in these processes become deactivated for one or more reasons. Where the accumulation of coke deposits causes the deactivation, reconditioning of the catalyst to remove coke deposits restores the activity of the catalyst. Coke is normally removed from catalyst by contact of the coke containing catalyst at high temperature with an oxygen-containing gas to combust and remove the coke in a regeneration process. These processes can be carried out in-situ or the catalyst may be removed from a vessel in which the hydrocarbon conversion takes place and transported to a separate regeneration zone for coke removal. Arrangements for continuously or semicontinuously removing catalyst particles from a reaction zone and for coke removal in a regeneration zone are well known.

In order to combust coke in a typical regeneration zone, a recycle gas is continuously circulated to the combustion section and a flue gas containing by-products of a coke combustion, oxygen, and water is continually withdrawn. Coke combustion is controlled by recycling a low oxygen concentration gas into contact with the coke-containing catalyst particles. The flue gas/recycle gas is continuously circulated through the catalyst particles. A small stream of makeup gas is added to the recycle gas to replace oxygen consumed in the combustion of coke and a small amount of flue gas is vented off to allow for the addition of the makeup gas. The steady addition of makeup gas and the venting of flue gas establishes a steady state condition that produces a nearly constant concentration of water and oxygen as well as the combustion products in the recycle gas.

In continuous or semi-continuous regeneration process, coke laden particles are at least periodically added and withdrawn from a bed of catalyst in which the coke is combusted. Regions of intense burning that extend through portions of the catalyst bed develop as the coke is combusted. After this intense burning the catalyst requires reconditioning to restore and re-disperse the noble metal, usually platinum, to its most highly catalytic state. Reconditioning for a dehydrogenation catalyst will include contact with a chloride containing compound, to redistribute the noble metal and replace the chloride that may be lost from the catalyst, followed by a drying step to reduce the moisture content of the catalyst and finally a reducing step to change the noble metal from various oxidized states to a reduced metallic condition. A preferred noble metal is platinum.

A number of environmental and operational problems have been associated with these catalyst reconditioning steps. Replacing chloride on the catalyst and re-dispersing platinum over the surface of the catalyst are both done in the presence of a chloride compound. However, the catalyst platinum re-dispersion benefits from a high chlorine environment whereas chloriding is usually effected more efficiently in the presence of hydrogen chloride. The chlorine and hydrogen chloride in the chloride contact zone are in equilibrium with the water and oxygen present therein. This equilibrium is skewed towards higher concentrations of hydrogen chloride. In order to provide adequate chlorine for re-dispersion of the platinum metal, the total concentration of hydrogen chloride must be relatively high. Maintaining the high hydrogen chloride environment adds to the expense of designing the regeneration zone by requiring the recycle of hydrogen chloride-containing gas. In most cases, this recycle of the gas is done by a closed loop system, a heater, a blower and associated piping. The expense of this equipment is compounded by the fact that exotic materials are needed to withstand a hydrogen chloride environment. Moreover, gas must be vented from the halogenation loop that circulates the hydrogen chloride containing gas. This vented gas has a high concentration of hydrogen chloride and must, therefore, be vented or treated in a way that avoids damage to equipment or the environment. Another drawback associated with the high hydrogen chloride environment is that there is often more hydrogen chloride uptake on the catalyst than is necessary or desired.

This invention provides a process for the dehydrogenation of hydrocarbons which incorporates a method of reactivating a noble metal catalyst that has been deactivated by the accumulation of coke on its surface during dehydrogenation and requires regeneration to remove coke and needs re-dispersion of the noble metal to provide adequate catalytic activity. This invention is particularly suited for catalysts that use platinum metals and maintain a chloride concentration on the catalyst particles. In such cases, the arrangement and operation of this process will improve the re-dispersion of platinum on the catalyst particles and allow a better control of the chloride content on the reconditioned catalyst particles. This invention can also reduce emissions and handling problems associated with hydrogen chloride containing gases and can reduce the overall expense of operating a dehydrogenation process with the concomitant reconditioning of catalyst particles used therein.

INFORMATION DISCLOSURE

U.S. Pat. No. 3,652,231 (Greenwood et al.) shows regeneration apparatus in which a constant-width movable bed of catalyst is utilized. The '231 patent also describes a continuous catalyst regeneration process which is used in conjunction with catalytic reforming of hydrocarbons. U.S. Pat. Nos. 3,647,680 (Greenwood et al.) and 3,692,496 (Greenwood et al.) also deal with regeneration of reforming catalyst. The teachings of patents ('231, '680, and '496) are hereby incorporated in full into this patent application.

U.S. Pat. No. 2,965,563 (Steffgen et al.) discloses a process for hydroforming (reforming) naphtha at a temperature in the range of 800° F. to 975° F. The '563 patent does not teach a process for the dehydrogenation of propane or butane at operating conditions, including a temperature range of 1100°–1225° F., which conditions are much more severe than those used in reforming and which result in rapid catalyst deactivation thereby requiring frequent and repeated regeneration cycles.

U.S. Pat. No. 4,647,549 (Greenwood) discloses that a catalyst is firstly subjected to coke removal, then to halogen treatment and then finally to a drying step.

U.S. Pat. No. 3,278,419 (Coe et al.) discloses a process for the reactivation of a hydroforming (reforming) catalyst by firstly contacting the catalyst with chlorine and water and subsequently removing coke deposits from the catalyst by burning the coke.

SUMMARY OF THE INVENTION

This invention is a process for the dehydrogenation of a hydrocarbon selected from the group consisting of propane and butane in the presence of a catalyst comprising platinum and a carrier material wherein the spent catalyst is reconditioned in a regeneration zone that uses in the following order a combustion zone, a drying zone and a metal re-dispersion zone to remove coke and recondition catalyst particles.

The improved dehydrogenation process is characterized by the use of a regeneration zone having a combustion zone which is followed by a drying zone to remove moisture from the catalyst particles before they enter the metal re-dispersion zone. By removing moisture upstream of the metal re-dispersion zone, a high chlorine concentration can be maintained in the metal re-dispersion zone without a high HCl concentration. The high chlorine content in the re-dispersion zone favors the re-dispersion of noble metals particularly platinum. Thus, by arranging the different catalyst reconditioning zones, in the aforementioned order, metal re-dispersion on the catalyst is improved while at the same time chlorine addition to the regeneration apparatus is reduced which in turn reduces the cost of the regeneration apparatus by reducing or eliminating the discharge of hydrogen chloride to the atmosphere and the pollution problems associated therewith.

The process of this invention further improves the operation of the regeneration process when used in conjunction with an oxygen-enriched gas stream. The operation of the metal re-dispersion zone is improved by passing an oxygen-enriched stream therein, which in combination with the reduction in water achieved in the aforementioned drying zone, keeps the equilibrium between hydrogen chloride and chlorine shifted toward chlorine production thereby providing a high chlorine environment with only a small addition of chloride containing compound to the metal re-dispersion zone.

Accordingly, in one embodiment, this invention is a dehydrogenation process characterized by reconditioning catalyst particles that contain a noble metal by removing coke from the catalyst particles. In a first step, catalyst particles containing a noble metal and having coke deposited thereon are contacted with an oxygen-containing gas to remove the coke by combustion. The catalyst particles are then contacted with dry, heated gas to remove water from the catalyst particles and produce dried catalyst particles. The dried catalyst particles are contacted with a re-dispersion gas that contains chlorine to re-disperse the noble metal and produce catalyst particles having a re-dispersed noble metal.

In a more detailed embodiment, this invention is a dehydrogenation process characterized by reconditioning a platinum-containing catalyst by removing coke deposits. The coke-containing catalyst particles are passed to a burn zone and contacted with a recycle gas that combusts coke from the catalyst and removes the coke deposits. Catalyst particles are passed from the burn zone to a drying zone to remove water from the catalyst particles by contact with a drying gas until the particles have a water concentration of less than 1 weight percent based on catalyst weight. The drying gas has a temperature in the range of from about 800° F. (426° C.) to about 1100° F. (593° C.) and an oxygen concentration of from 21 to 39 mole percent. The catalyst particles are passed from the drying zone to a re-dispersion zone and contacted therein with a re-dispersion gas that contains chlorine and has an oxygen concentration of from 21 to 35 mole percent. Contact with the re-dispersion gas re-disperses the platinum metal on the catalyst particles. The catalyst particles are passed from the re-dispersion zone to a reduction zone wherein the catalyst particles are contacted with a hydrogen-rich gas at a temperature of from about 800° F. (426° C.) to about 1000° F. (538° C.) and a pressure of from about 5 psig (34.5 kPa gauge) to about 125 psig (862 kPa gauge). The reconditioned catalyst particles are recovered from the reduction zone for further catalytic use.

Another embodiment of the present invention may be characterized as a process for the dehydrogenation of a hydrocarbon selected from the group consisting of propane and butane in the presence of a catalyst comprising platinum and a carrier material wherein the dehydrogenation is conducted at severe operating conditions which promote rapid deactivation of the catalyst including the agglomeration of the platinum on the carrier material and the deposition of coke on the catalyst, the improvement which comprises the steps of contacting the catalyst comprising platinum and a carrier material having coke deposited thereon with an oxygen containing gas to remove the coke by combustion; contacting the catalyst having coke removed therefrom with a drying gas having a temperature in a range of from about 800° F. (426° C.) to about 1100° F. (593° C.) and an oxygen concentration from about 21 to about 39 mole percent until the catalyst has a water concentration of less than about 1 weight percent; contacting the catalyst comprising platinum and a carrier material having a water concentration of less than about 1 weight percent with a re-dispersion gas comprising chlorine and having an oxygen concentration from about 21 to about 39 mole percent to re-disperse platinum on the catalyst; contacting the resulting catalyst having re-dispersed platinum in a reduction zone with a hydrogen-rich gas at a temperature from about 900° F. (482° C.) to about 950° F. (510° C.) and a pressure from about 5 psig (34.5 kPa gauge) to about 125 psig (862 kPa gauge); and recovering reconditioned catalyst from the reduction zone.

In yet another embodiment, this invention is an apparatus for the regeneration of catalyst particles. The apparatus includes a vessel that has an upper and a lower section, a recycle gas inlet nozzle and a flue gas outlet nozzle that are located in the upper section, a drying gas inlet nozzle and re-dispersion gas inlet nozzle located in the lower section of the vessel, a catalyst particle inlet nozzle in an upper portion of the vessel and a catalyst particle outlet nozzle in a lower portion of the vessel. Inside the vessel, there is located an inlet retention screen and an outlet retention screen that are spaced apart to define a vertically extending catalyst particle bed. The catalyst particle bed has direct communication with the catalyst particle inlet nozzle and a lower outlet for transferring catalyst particles from the bed to the lower section of the vessel. The inlet retention screen defines, at least in part, a distribution space that communicates with the recycle gas inlet nozzle and distributes the gas entering thereby. A gas collection space is defined in part by the outlet screen and communicates with the flue gas outlet nozzle. The vessel also defines a drying zone and a re-dispersion zone. The drying zone is located in an upper portion of the lower section of the vessel and includes means for distributing a drying gas about the drying zone. The means for distributing the drying gas is in communication with the drying gas inlet nozzle. The re-dispersion zone is located below the drying zone and above the catalyst particle outlet nozzle. Means are also provided in the drying zone for distributing a re-dispersion gas about the re-dispersion zone. The means for distributing the re-dispersion gas are in communication with the re-dispersion gas inlet nozzle.

Other objects, embodiments and advantages of this invention are discussed in the following detailed description.

DETAILED DESCRIPTION OF THE INVENTION

Figure 1:
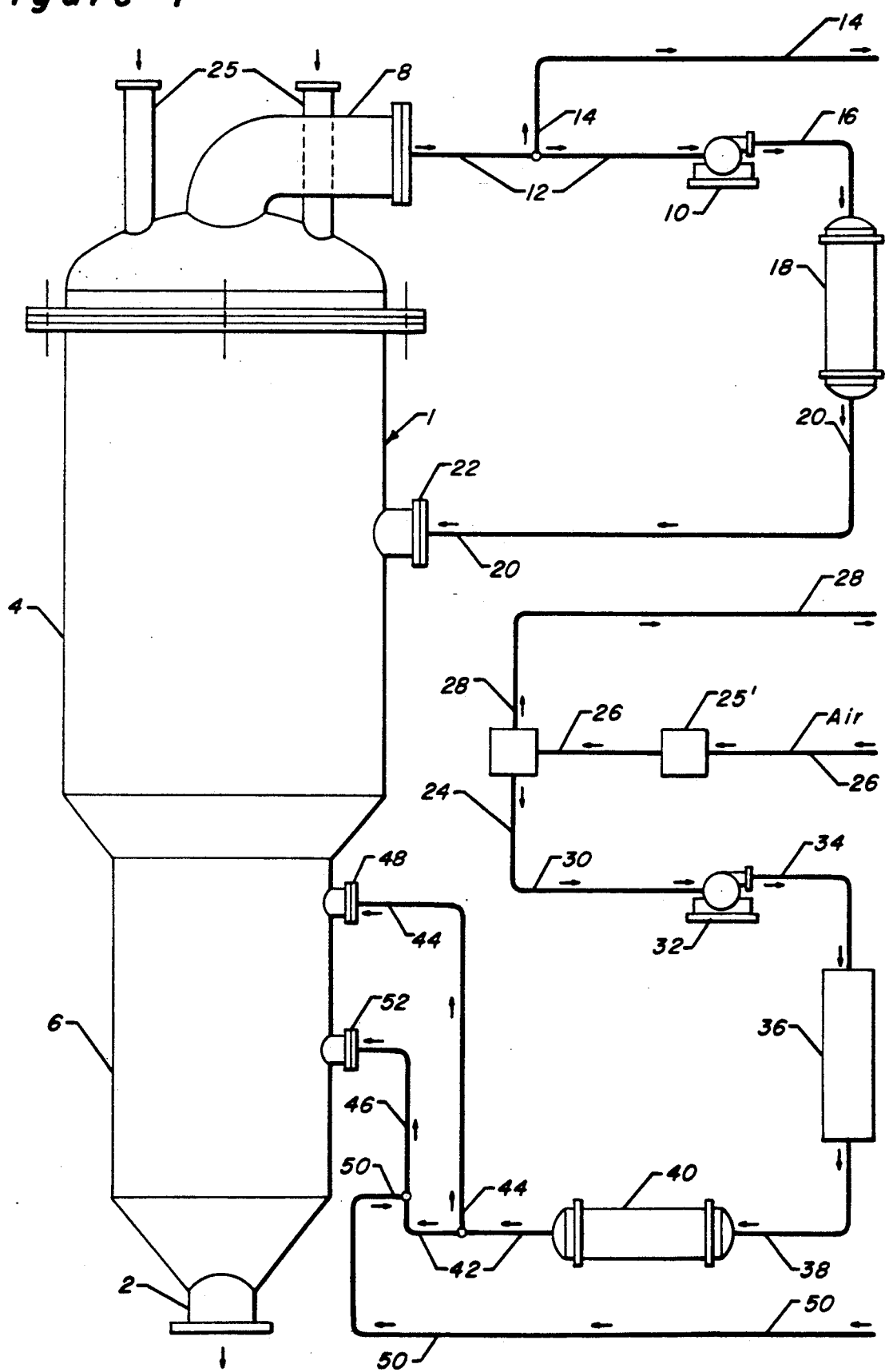
FIG. 1 is a schematic illustration of a regeneration zone arranged in accordance with this invention and some of the equipment associated therewith.

This invention is a process for the catalytic dehydrogenation of a hydrocarbon selected from the group consisting of propane and butane. Catalytic dehydrogenation is an established hydrocarbon conversion process employed in the petroleum processing industry for producing olefin hydrocarbons from paraffin hydrocarbon feedstock. The art of catalytic dehydrogenation is well known and does not require detailed description herein.

Briefly, in catalytic dehydrogenation, a feedstock is admixed with a recycle stream comprising hydrogen and contacted with catalyst in a reaction zone. Preferred feedstock for catalytic dehydrogenation is a petroleum fraction comprising paraffins having from about 3 to about 18 carbon atoms. The catalytic dehydrogenation process is particularly applicable to the treatment of hydrocarbon feedstocks containing substantially paraffinic hydrocarbons which are subject to dehydrogenation reactions to thereby form olefinic hydrocarbon compounds. In accordance with the present invention, the hydrocarbon feedstock is selected from the group consisting of propane and butane.

A catalytic dehydrogenation reaction is normally effected in the presence of catalyst particles comprised of one or more Group VIII noble metals (e.g., platinum, iridium, rhodium, palladium) combined with a porous carrier, such as a refractory inorganic oxide. Alumina is a commonly used carrier. The preferred alumina materials are known as the gamma, eta and theta alumina with gamma and eta alumina giving the best results. An important property related to the performance of the catalyst is the surface area of the carrier. Preferably, the carrier will have a surface area of from 100 to about 500 m$^2$/g. It has been discovered that removal of moisture from a combustion zone of a regeneration zone will produce a more than linear increase in the life of a typical dehydrogenation catalyst. The particles are usually spheroidal and have a diameter of from about 1/16th to about ⅛th inch (1.5–3.1 mm), though they may be as large as ¼th inch (6.35 mm). In a particular regenerator, however, it is desirable to use catalyst particles which fall in a relatively narrow size range. A preferred catalyst particle diameter is 1/16th inch (1.5 mm). Generally, the catalyst particles have a chloride concentration of between 0.5 and 3 weight percent. During the course of a dehydrogenation reaction, catalyst particles become deactivated as a result of mechanisms such as the deposition of coke on the particles; that is, after a period of time in use, the ability of catalyst particles to promote dehydrogenation reactions decreases to the point that the catalyst is no longer useful. The catalyst must be reconditioned, or regenerated, before it can be reused in a dehydrogenation process.

In preferred form, the dehydrogenation process will employ a moving bed reaction zone and regeneration zone. The present invention is applicable to a moving bed regeneration zone and a fixed bed reaction zone. Fresh catalyst particles are fed to a reaction zone, which may be comprised of several subzones, and the particles flow through the zone by gravity. Catalyst is withdrawn from the bottom of the reaction zone and transported to a regeneration zone where a hereinafter described multi-step regeneration process is used to recondition the catalyst to restore its full reaction promoting ability. Catalyst flows by gravity through the various regeneration steps and then is withdrawn from the regeneration zone and furnished to the reaction zone. Movement of catalyst through the zones is often referred to as continuous though, in practice, it is semi-continuous. By semi-continuous movement is meant the repeated transfer of relatively small amounts of catalyst at closely spaced points in time. For example, one batch per minute may be withdrawn from the bottom of a reaction zone and withdrawal may take one-half minute, that is, catalyst will flow for one-half minute. If the inventory in the reaction zone is large, the catalyst bed may be considered to be continuously moving. A moving bed system has the advantage of maintaining production while the catalyst is removed or replaced.

When using the process of this invention in a batch, continuous, or semi-continuous catalyst regeneration process, catalyst is contacted with a hot oxygen-containing gas stream (known as recycle gas) in order to remove coke which accumulates on surfaces of the catalyst while it is in a dehydrogenation reaction zone. Coke is comprised primarily of carbon but is also comprised of a relatively small quantity of hydrogen. The mechanism of coke removal is oxidation to carbon monoxide, carbon dioxide, and water. Coke content of spent catalyst may be as much as 20% of the catalyst weight, but 5–7% is a more typical amount. Within the combustion zone, coke is usually oxidized at temperatures ranging from about 850° F. (471° C.) to about 1000° F. (538° C.), but temperatures in localized regions may reach 1100° F. (593° C.) or more.

Oxygen for the combustion of coke enters what is called a combustion section of the regeneration zone in what has been termed a recycle gas. The recycle gas contains a low concentration of oxygen usually on the order of 0.5 to 1.5% by volume. The arrangement of a typical combustion section may be seen in U.S. Pat. No. 3,652,231. As the coke is combusted, the small amount of hydrogen within the coke reacts with the oxygen to form water. Flue gas made up of carbon monoxide, carbon dioxide, water, unreacted oxygen, chlorine, hydrochloric acid, nitrous oxides, sulfur oxides and nitrogen is collected from the combustion section and withdrawn from the regeneration zone as flue gas. Thus, the recycle gas and flue gas form a recycle gas loop wherein flue gas is continually withdrawn from the process mixed with an oxygen-containing gas to replenish consumed oxygen and returned to the combustion section as recycle gas. A small amount of the flue gas is vented off from the process to allow the addition of an oxygen-containing gas called makeup gas. The oxygen-containing gas is combined with the flue gas to replace the oxygen consumed by the coke combustion and the combined gas is recycled to the combustion section. In the past, the oxygen-containing gas was typically air. The amount of air needed in past regeneration processes to replenish the oxygen consumed during the coke combustion is relatively small, usually about 3% of the volumetric rate of the recycle gas stream.

All of the oxygen supplied to an upper region of the bed is consumed, since an abundant amount of coke is present. As catalyst particles move downward in the bed and coke is removed, a point is reached where less than all of the oxygen delivered is consumed. This is termed the breakthrough point. Typically, breakthrough occurs at a location spaced about half the distance down the total length of the bed in the combustion section. It is known to those skilled in the art that catalyst particles of the type used in the hydrocarbon conversion processes of this invention have a large surface area, which results from the existence of a multiplicity of pores. When the catalyst particles reach the breakthrough point in the bed, the coke left on the surface of the particles is deep within the pores and therefore the oxidation reaction occurs at a much slower rate.

Reiterating, the combustion of coke also produces water. The only place for the water to escape from the combustion step is in the small amount of vented flue gas. Therefore, the water concentration in the recycle loop increases until the difference between the amount of water entering with the makeup gas stream and the amount of water leaving with the vent stream equal the amount of water produced during the combustion of coke and equilibrium is reached. The water circulating within the recycle gas loop created a constant steam concentration during the coke combustion process. The water concentration in the recycle loop could be lowered by drying the air that made up the makeup gas, installing a drier for the gas circulating in the recycle gas loop or venting a larger amount of gas from the recycle gas stream to lower the water equilibrium in the recycle gas loop.

In accordance with this invention the catalyst particles pass from the combustion zone directly into a drying zone where the water that is left on the catalyst particles after the combustion process is removed. Water is evaporated from the surface and pores of the catalyst particles by contact with a heated gas stream. Any gas stream that can absorb water from the catalyst particles can be used in the drying zone. The drying gas in the past has typically been air which after heating to a temperature of between 800° F. (426° C.) and 1100° F. (593° C.) can reduce the moisture content of the catalyst particles to acceptable levels. Drying of the air stream before it is heated will increase the adsorbability of water from the catalyst particles and decrease the size of the drying zone. It is preferable that the drying gas stream contain oxygen so that any final residual burning of coke from the inner pores of catalyst particles may be accomplished in the drying zone, and any excess oxygen that is not consumed in the drying zone can pass upwardly with the flue gas from the combustion zone to replace the oxygen that is depleted through the combustion reaction. In a preferred form of this invention, the drying gas will have an oxygen-concentration that is at least roughly equal to that of air. In a preferred embodiment, all or a portion of the drying gas will be oxygen-enriched so that there will be a high oxygen concentration in the drying zone that will promote complete combustion of any residual coke left in the catalyst. Contact of the catalyst particles with a gas containing a high concentration of oxygen also aids in restoring full activity to the catalyst particles by raising the oxidation state of the platinum contained thereon. The drying zone should be designed to reduce the moisture content of the catalyst particles to at least 0.01 weight fraction based on catalyst before the catalyst particles leave the drying zone. Preferably, the catalyst particles will have a water content of between 0.005 to 0.007 weight fraction before passing to the re-dispersion zone. The gas entering the drying zone will generally be kept at a temperature of between about 800° F. (426° C.) and 1100° F. (593° C.).

Following drying, the catalyst is contacted with a chlorine-containing gas to re-disperse the platinum over the surface of the catalyst. This re-dispersion step typically takes place in a separate zone located below the drying zone. Exposure to reactants in a wet reduction zone and the exposure to high temperatures and steam in the combustion zone serves to agglomerate the platinum on the surface of the catalyst. Once the coke has been removed and the catalyst particles are in various states of oxidation, contact of the catalyst at a temperature between about 800° F. (426° C.) and 1100° F. (593° C.) in a chlorine environment will re-disperse the platinum over the surface of the catalyst support. Temperature within the re-dispersion zone will usually be in a range of about 950° F. (510° C.) to about 1000° F. (538° C.). A high concentration of chlorine, on the order of 0.01 to 0.2 mole percent of the gas in the re-dispersion zone, is highly beneficial to promoting rapid and complete re-dispersion of the platinum metal.

The re-dispersion step is carried out in the presence of chlorine and an oxygen atmosphere. An oxygen atmosphere is generally employed and desired in carrying out the re-dispersion step. The presence of oxygen aids in the re-dispersion of the metallic catalyst components on the carrier. A lower water concentration in the environment of the re-dispersion section also facilitates the re-dispersion by maintaining a high chlorine concentration in the re-dispersion zone. The concentration of chlorine in the re-dispersion section is governed by the Deacon equilibrium equation.

$$HCl + O_2 \rightleftharpoons H_2O + Cl_2$$

Therefore, to the extent that the catalyst entering the re-dispersion section has a lower water concentration, it will favor the shift to the right of the equation, thereby producing more chlorine for the re-dispersion step. Since oxygen aids in the re-dispersion of platinum, additional benefits are obtained by the method of this invention when an oxygen-enriched stream is passed into the re-dispersion section to increase the oxygen concentration and further promote the re-dispersion of the catalytic metal on the carrier. Therefore, in its preferred form, an oxygen-enriched stream will be combined with a chlorine gas and distributed in the re-dispersion zone. The low water content and the high oxygen concentration will prevent a loss in a chlorine concentration by preventing an equilibrium shift to the left that would produce hydrogen chloride. By shifting the equilibrium equation to the production of chlorine instead of hydrogen chloride, a high chlorine concentration may be obtained in the re-dispersion zone.

The re-dispersion gas will usually exit the re-dispersion zone by entering the drying zone. As the chlorine-containing re-dispersion gas leaves the drying zone with the drying gas and comes into contact with water on the catalyst that is entering the drying zone, the equilibrium reaction will again again favor the production of hydrogen chloride. As a result, essentially all of the chloride that leaves the re-dispersion zone will eventually be converted to hydrogen chloride once it is passed through the drying zone. In a typical arrangement, the re-dispersion gas and drying gas will become mixed with the flue gas that is passing through the combustion zone. Therefore, once again, hydrogen chloride resulting from the presence of chlorides in a treatment zone will be present in the flue gas from the regeneration process. However, because of the much lower overall chloride concentration needed in the re-dispersion zone to produce a high chlorine environment, the amount of hydrogen chloride now present in the flue gas will be in concentrations that will raise few metallurgical problems with process equipment and will necessitate minor, if any, treatment in the gas vented from the flue gas. Since in previous practice the hydrogen to chlorine ratio was 13 to 1, this invention by reversing the equilibrium conditions within the re-dispersion zone can provide more than a ten-fold decrease in the amount of chlorides that exit the re-dispersion zone while providing an environment with an equivalent chlorine concentration.

After the platinum has been re-dispersed on the catalyst, it is passed to a reduction zone. Re-dispersed catalyst from the re-dispersion zone must be reduced to change the platinum on the catalyst to an elemental state by reduction. Consequently, in most processes, the catalyst will be contacted with a hydrogen-rich reduction gas before being used for catalytic purposes. Reduction of the highly oxidized catalyst with a relatively pure hydrogen reduction gas will restore essentially all of the catalytic activity to the platinum metal. The hydrogen-rich reduction gas will typically have a hydrogen concentration of about 85 mole percent. The hydrogen gas will contact the catalyst at a temperature from about 900° F. (482° C.) to about 950° F. (510° C.). Although reduction of the oxidized catalyst is an essential step in most dehydrogenation operations, the step is usually performed just ahead or within the reaction zone and is not generally considered a part of the apparatus for the regeneration process.

A preferred embodiment of this invention uses an oxygen-enriched air stream for the catalyst treatment zone. A number of processes are known for enriching air streams with oxygen. These processes can use selective adsorbents, gas permeable membranes or a combination of both to generate such streams. One such process that uses a gas permeable membrane to enrich an oxygen stream and produce a non-permeate stream with an increased nitrogen concentration is shown in U.S. Pat. No. 4,787,919. The teachings of which are herein incorporated by reference. Additional diffusion membranes for the separation of gases are also shown in U.S. Pat. No. 3,830,733. The teachings of which are herein incorporated by reference. These and other commercially available processes can economically produce oxygen-enriched gas streams having concentrations of 39 mole percent. Air separation processes are beneficial since they provide oxygen-enriched streams that can be used in the treatment steps of the regeneration zone. Nevertheless, this invention does not require the use of any particular source of oxygen-enriched gas streams for use in the conditioning steps.

Figure 2:
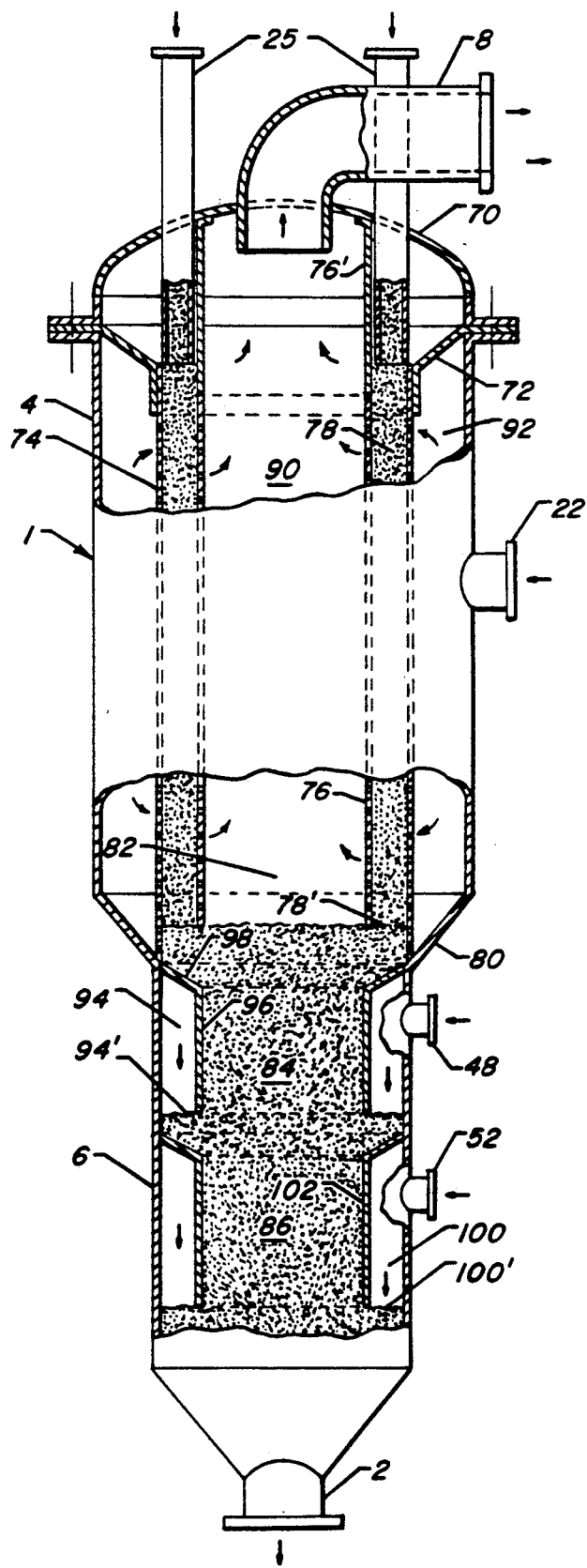
FIG. 2 is a partial cross-sectional elevation of the regeneration zone shown in FIG. 1.

The specific arrangement and operation of a regeneration process can be better understood by reference to FIGS. 1 and 2. These Figures will be used to describe an example of a particular application of this process in the reconditioning of dehydrogenation catalyst. The description of this invention in the context of a specific example and regeneration zone arrangement is not intended to limit the broad scope of the invention as presented in the claims. The drawings show only elements and equipment which are essential to a clear understanding of the invention. Application and use of additional required items is well within the purview of one skilled in the art. U.S. Pat. Nos. 3,652,231; 3,647,680 and 3,692,496, which have been previously mentioned, may be consulted for additional detailed information. Numerical data provided in this example such as stream compositions, flow rates, component concentrations, temperatures and pressures have been calculated in full or in part using engineering calculation and data from related regeneration processes.

Referring now to FIG. 1, spent catalyst particles containing 5 weight percent coke are introduced into regeneration vessel 1 by means of nozzles 25. Catalyst is removed from regeneration vessel 1 at the lower end through nozzle 2. Regeneration vessel 1 has an upper section 4 and a lower section 6. Nozzle 2 removes reconditioned catalyst from regeneration vessel 1 and the process.

Flue gas having an oxygen concentration of approximately 0.7 mole percent and a hydrogen chloride concentration of approximately 160 ppm leaves the upper section of the regeneration vessel 1 through nozzle 8. Flue gas exiting through nozzle 8 is conveyed to blower 10 by pipeline 12. Approximately 3 weight percent of the flue gas leaving the regeneration vessel 1 through pipeline 12 is vented from the system by pipeline 14. The recycle gas from blower 10 is carried by line 16 and passes through heater 18. Heater 18 heats the recycle gas to carbon-burning temperatures during start-up and, if necessary, adds heat to the recycle stream during normal operation. Recycle gas leaving heater 18 through pipeline 20 enters regeneration vessel 1 through nozzle 22. Pipelines 12, 16 and 20 together with a hereinafter described combustion section form a recycle loop.

A gas separation system 24 supplies make-up gas to the recycle loop. Air from drier 25 enters gas separation system 24 by a pipeline 26. Separation system 24 produces an oxygen-deficient gas stream, carried by pipeline 28 and an oxygen-enriched gas stream carried by a pipeline 30. The oxygen-enriched gas is added to regeneration vessel 1 at a rate of addition generally equal to the rate of the gas venting from pipeline 14.

Oxygen-enriched air from line 30 is taken into blower 32. Blower 32 discharges oxygen-enriched air into line 34 and through a drier 36 that reduces the moisture content of the oxygen-enriched air. Dry air is passed by line 38 into a heater 40 that raises the temperature of the oxygen-enriched air to about 1000° F. Dry heated air is taken by line 42 and divided between a line 44 and a line 46. Approximately 50 volume percent of the oxygen-enriched air is taken by line 44 and delivered to a hereinafter described drying zone through nozzle 48. The remainder of the enriched air in line 46 is mixed with a chlorine stream from line 50 that gives the contents of line 46, a chlorine concentration of about 0.11 mole percent. The chlorine and dry heated air enter a hereinafter described platinum re-dispersion zone through a nozzle 52. Although in this arrangement, the oxygen-enriched stream discharged from the heater is split between the drying zone and the re-dispersion zone, other regenerator arrangements may transfer all of the oxygen-enriched gas from line 42 directly into the re-dispersion zone.

The various zones and the arrangement of the internals in the regeneration vessel can be more fully appreciated from FIG. 2. Looking first at the flow of catalyst particles, nozzles 25 pass through the upper head 70 of regeneration vessel 1. The nozzles discharge catalyst particles into an annular catalyst bed 78 formed by an outer catalyst retention screen 74 and an inner catalyst particle retention screen 76. Retention screens 74 and 76, in this embodiment, are cylindrical in form and concentric with the center line of regeneration vessel 1. Retention screens 74 and 76 are perforated with holes that are large enough to allow gas to pass through the annular catalyst bed but not permit the passage of catalyst particles therethrough. Outer catalyst particle retention screen 74 extends downward from the bottom of nozzle 25 to a swedge section 80 of regeneration vessel 1. Angled supports 72 guide the top of screen 74 and keep it centered in regeneration vessel 1. Inner catalyst retention screen 76 is attached to the top head of regeneration vessel 1 and extends downward therefrom to a point slightly above the lower end of outer catalyst screen 74. The bottom 78' of the annular catalyst particle bed 78 is open to allow catalyst particles to empty from the catalyst bed into a central portion 82 of regeneration vessel 1. From about the bottom of opening 78', the catalyst particles fill the lower section 6 of regeneration vessel 1. The upper volume of catalyst particles in the lower section 6 is located in a drying zone that is generally denoted as 84. Catalyst particles in the lower portion of vessel 6 generally denoted by the number 86 are in a re-dispersion zone. Catalyst particles in section 86 are statically supported by catalyst particles that extend through the end closure of lower section 6. The catalyst particles are periodically transferred by withdrawing a predetermined volume of catalyst from nozzle 2 which in turn allows all the catalyst particles to travel downward through the previous described zones.

As the catalyst particles travel downward through the regeneration process, they pass first through a combustion zone 90 that includes the previously described annular catalyst bed 78. Recycled gas that enters the combustion zone through nozzle 22 is distributed in an annular chamber 92 that extends around the outer catalyst particle retention screen and is defined on its sides by outer particle retention screen 74 and the vessel wall of upper vessel section 4 and its bottom by swedge section 80. An upper portion 76' of inner particle retention screen 76 is impervious to gas flow, or blanked off to prevent gas flow from chamber 92 across the top of the vessel. As the recycle gas passes through catalyst bed 78, oxygen is consumed in the combustion of coke and flue gas is collected in central section 82. Flue gas in central section 82 is transported out of the regeneration vessel head 70 by nozzle 8.

Catalyst below combustion zone 90 is contacted with a drying gas. The drying gas enters the drying zone through nozzle 48. Nozzle 48 communicates with an annular volume 94 that distributes fluidizing gas. Distribution volume 94 is formed by a baffle having a vertically extended cylindrical section 96 that is concentrically located with respect to the regeneration vessel 1. The upper portion of the baffle consists of a frusto-conical section 98 that is attached to the lower section of swedge 80 and supports the upper end of cylindrical section 96. The bottom 94' of annular distributing volume 94 is open and drying gas flows outward into the drying zone around the entire circumference of cylinder 96. The relative duration of catalyst particles within the drying zone for a given catalyst circulation rate is determined principally by the vertical length of cylindrical section 96. The catalyst particles remain in the drying zone for approximately 2 hours and leave the bottom of the drying zone having a water content of approximately 0.6 weight percent.

The structural design of re-dispersion zone 86 is essentially the same as that of the drying zone. Previously described chlorine containing re-dispersion gas enters, via nozzle 52, an annular volume 100 that distributes the re-dispersion gas. Distributing volume 100 is defined by the wall of lower vessel section 6 and a baffle consisting of another concentric cylinder 102 that is secured to the lower vessel by frusto-conical section 104. Again an open bottom 100' allows re-dispersion gas to be distributed about the entire circumference of the annular distributing volume 100 and about the re-dispersion zone 86. Catalyst duration within the re-dispersion zone is also governed principally by the length of cylindrical section 102. In this example, the re-dispersion zone has a sufficient length to provide approximately a 2 hour residence time for the particles located therein.

Those skilled in the art will recognize that the regeneration section described by FIGS. 1 and 2 is relatively simple in comparison to those previously employed for the reconditioning of dehydrogenation catalyst. The regeneration section achieves a virtually complete removal of coke from the catalyst while also obtaining a good re-dispersion of platinum metals. All of these conditioning steps are obtained with a very minimal discharge of chloride compound from the regeneration zone. This new arrangement only relies on one recycle loop to return flue gas to the combustion zone. Therefore, this invention offers a simplified arrangement for a catalyst regeneration zone that provides a superior reconditioning of the catalyst with reduced emission problems and equipment cost.

What is claimed is:

1. In a process for the dehydrogenation of a hydrocarbon selected from the group consisting of propane and butane in the presence of a catalyst comprising platinum and a carrier material wherein said dehydrogenation is conducted at severe operating conditions which promote rapid deactivation of said catalyst including the agglomeration of said platinum on said carrier material and the deposition of coke on said catalyst, the improvement which comprises the steps of contacting said catalyst comprising platinum and a carrier material having coke deposited thereon with an oxygen containing gas to remove said coke by combustion; contacting said catalyst having coke removed therefrom with a drying gas having a temperature in a range of from about 800° F. (426° C.) to about 1100° F. (593° C.) and an oxygen concentration from about 21 to about 39 mole percent until said catalyst has a water concentration of less than about 1 weight percent; contacting said catalyst comprising platinum and a carrier material having a water concentration of less than about 1 weight percent with a re-dispersion gas comprising chlorine and having an oxygen concentration from about 21 to about 39 mole percent to re-disperse platinum on said catalyst; contacting the resulting catalyst having re-dispersed platinum in a reduction zone with a hydrogen-rich gas at a temperature from about 900° F. (482° C.) to about 950° F. (510° C.) and a pressure from abut 5 psig (34.5 kPa gauge) to about 125 psig (862 kPa gauge); and recovering reconditioned catalyst from said reduction zone.

2. The process of claim 1 wherein said catalyst is continuously withdrawn and delivered to a dehydrogenation zone.

* * * * *